(12) United States Patent
Laux

(10) Patent No.: US 7,524,188 B2
(45) Date of Patent: Apr. 28, 2009

(54) IMPLANT PART FOR A DENTAL IMPLANT

(75) Inventor: Thomas Laux, Steppach/Neusäss (DE)

(73) Assignee: Paraplant 2000 OHG, Hamburg (DE)

( * ) Notice: Subject to any disclaimer, the term of this patent is extended or adjusted under 35 U.S.C. 154(b) by 33 days.

(21) Appl. No.: 11/177,165

(22) Filed: Jul. 9, 2005

(65) Prior Publication Data
US 2005/0250072 A1    Nov. 10, 2005

Related U.S. Application Data

(63) Continuation-in-part of application No. PCT/DE2004/001699, filed on Jul. 29, 2004.

(30) Foreign Application Priority Data
Aug. 5, 2003  (DE) ................. 103 36 537

(51) Int. Cl.
*A61C 8/00* (2006.01)
(52) U.S. Cl. .................... 433/173; 433/169
(58) Field of Classification Search ......... 433/172–176, 433/169
See application file for complete search history.

(56) References Cited

U.S. PATENT DOCUMENTS

| 4,575,340 A | * | 3/1986 | Lustig | 433/173 |
| 4,793,808 A | * | 12/1988 | Kirsch | 433/173 |
| 5,033,962 A | * | 7/1991 | Scatena | 433/169 |
| 5,082,445 A | * | 1/1992 | Singer | 433/169 |
| 5,890,902 A | * | 4/1999 | Sapian | 433/173 |

FOREIGN PATENT DOCUMENTS

DE    10149166 C1  *  2/2003

\* cited by examiner

*Primary Examiner*—John J Wilson
(74) *Attorney, Agent, or Firm*—Klaus J. Bach

(57) ABSTRACT

In a dental implant comprising a mounting post, a crown supported on the mounting post and a spring element supported between the mounting post and the crown so that the crown is movable within limits in axial direction relative to the mounting post against the force of the spring element, the crown is a single part and connected to the mounting post by a form locking connection while the spring element is effective directly between the mounting post and the crown.

2 Claims, 5 Drawing Sheets

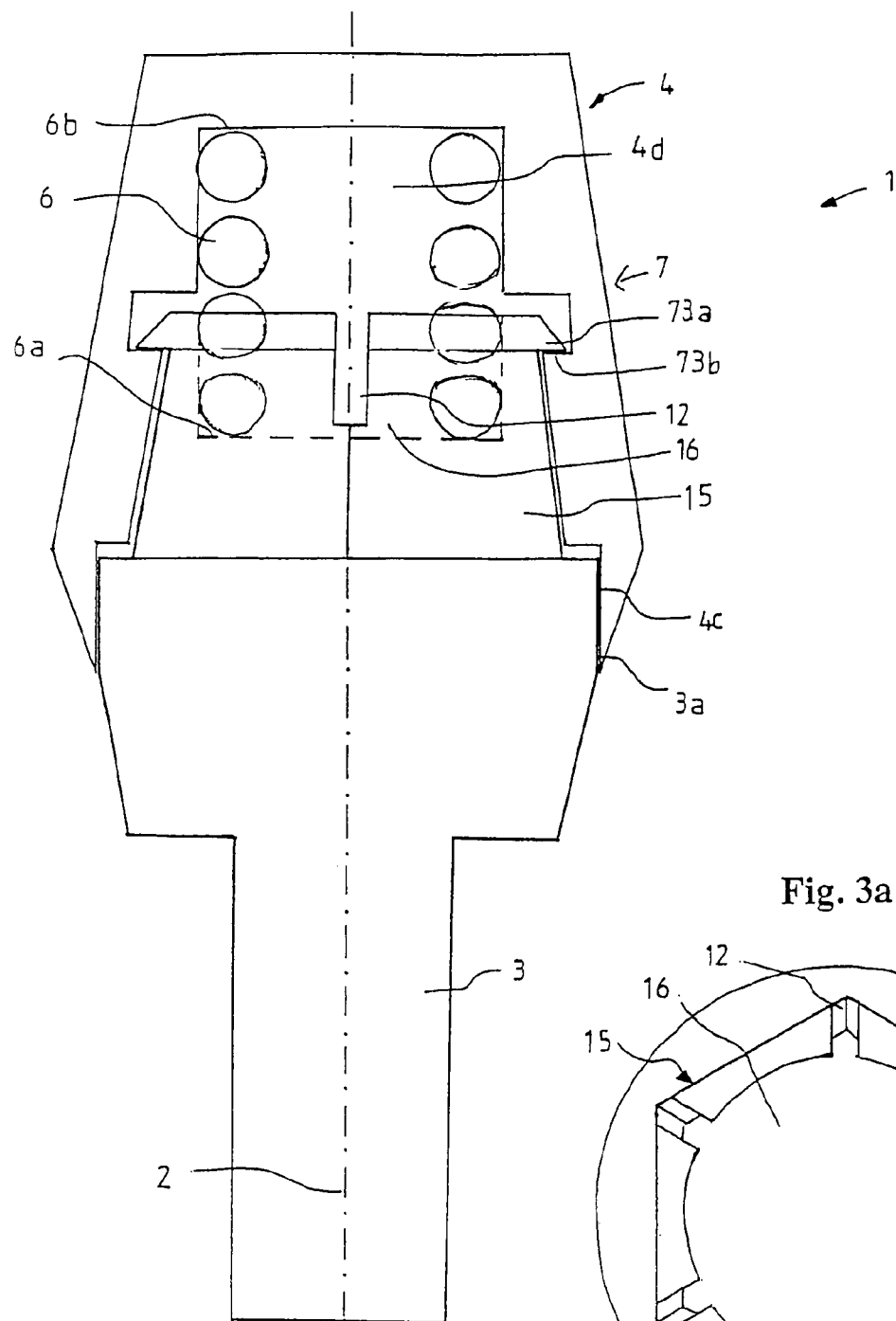
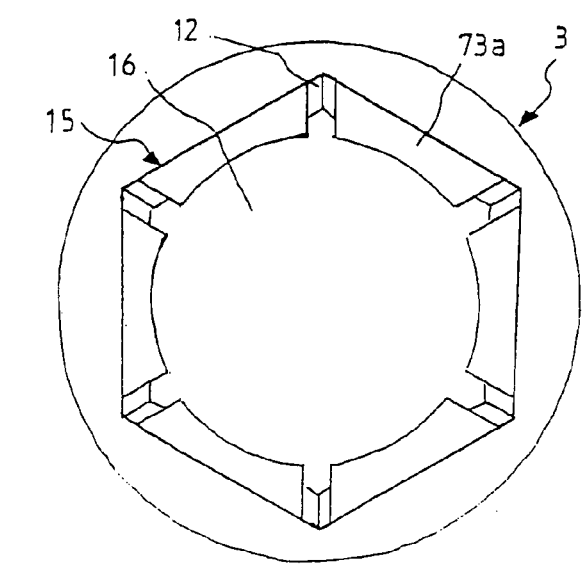
Fig. 3
Fig. 3a

IMPLANT PART FOR A DENTAL IMPLANT

This is a Continuation-In-Part Application of International Application PCT/DE2004/001699 filed Jul. 29, 2004 and claiming the priority of German Application 103 36 537.0 filed Aug. 5, 2003.

BACKGROUND OF THE INVENTION

The invention relates to an implant part for a dental implant with a mounting post and a crown which is displaceable in axial direction within limits against the force of a spring.

Such an implant part for a dental implant is disclosed in DE 101 49 166 C1. The dental implant part disclosed therein comprises a basic carrier implanted into the jaw bone, a hollow cylindrical mounting post and a two-part secondary crown. The mounting post is attached to the basic carrier by means of a central connecting bolt which extends through the hollow cylindrical mounting post. On the mounting post, the two-part secondary crown is disposed. In order to permit a translatory movement in the longitudinal direction of the dental implant, the secondary crown comprises two separate sections which however are interconnected, that is, a support part and a connecting part between which two spring elements are arranged for shock damping. It is the object of this dental implant to provide for a secure and durable connection without detrimentally affecting the damping effects. It is however a disadvantage of this dental implant that the assembly of the two part secondary crown and the spring elements disposed therein is complicated and time consuming.

Furthermore, the central bore in the mounting post reduces its strength whereby the installation of the mounting post on the basic carrier becomes more difficult.

It is the object of the present invention to provide an implant part for a dental implant which is simple and can easily be manufactured and which is also easy to install and provides for a durable and secure connection of the implant parts of the dental implant without detrimentally affecting the resiliency provided by damping springs disposed in the implant.

SUMMARY OF THE INVENTION

In a dental implant part comprising a mounting post, a crown supported on the mounting post and a spring element supported between the mounting post and the crown so that the crown is movable within limits in axial direction relative to the mounting post, the crown is a single part and connected to the mounting post by a form locking connection while the spring element is effective directly between the mounting post and the crown.

The invention will be described below in greater detail with reference to the accompanying drawings.

BRIEF DESCRIPTION OF THE DRAWINGS

FIG. 3a is a top view of the mounting post for a dental implant shown in FIG. 3.

DESCRIPTION OF PREFERRED EMBODIMENTS

Figures 1, 1A:
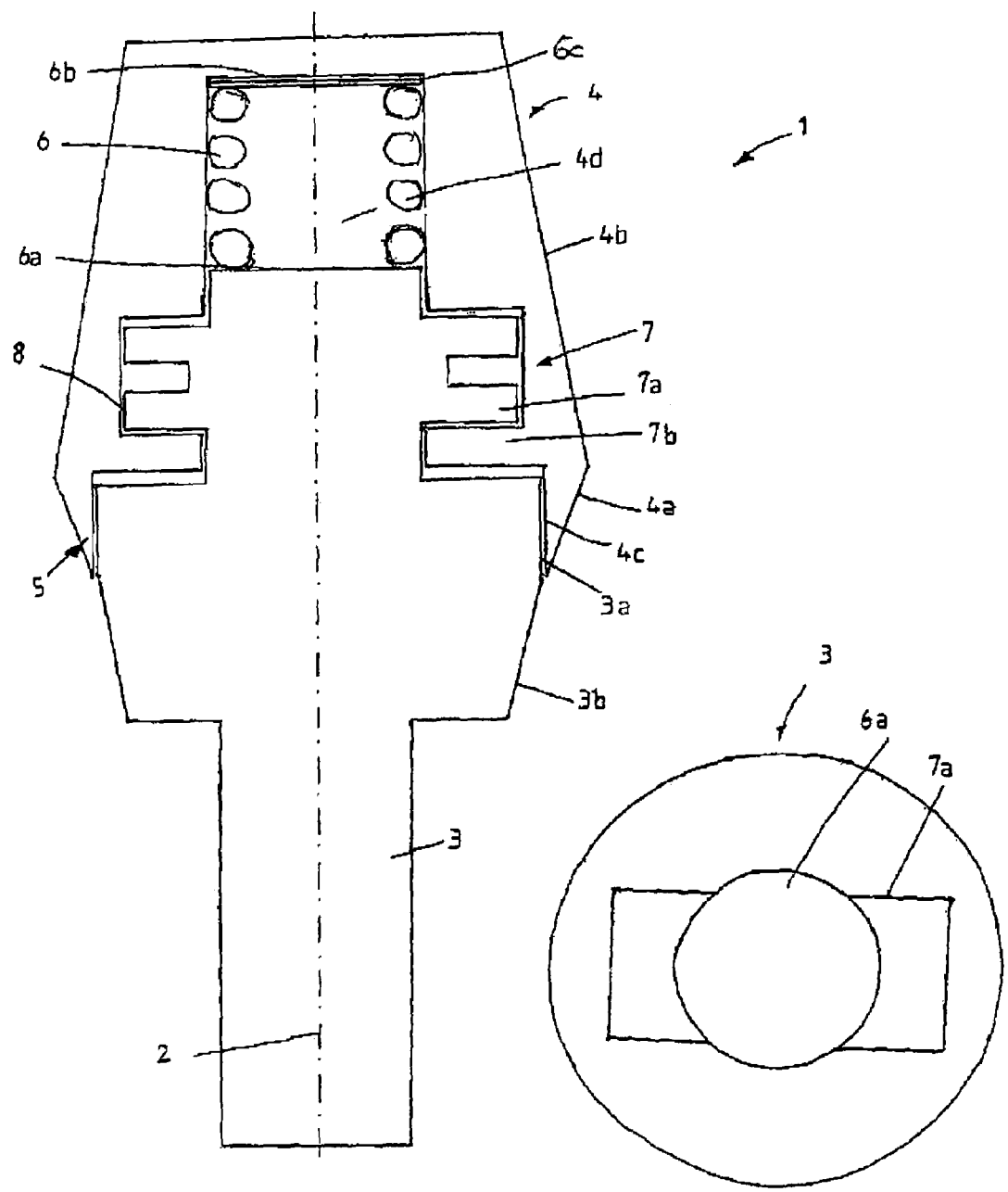
FIG. 1 is a cross-sectional view of a dental implant with an implant part mounted via bayonet locking structure.
FIG. 1a is a top view of a mounting post for the implant part.

FIG. 1 is a cross-sectional view along the longitudinal axis 2 of a composite dental implant 1 and FIG. 1a is a top view of the corresponding mounting post 3. The terms "top" and "bottom" used in the following description refer to the longitudinal axis 2 of an implant 1 as shown in FIGS. 1, 2, 3, 4, and 5 installed in a lower jaw bone.

The mounting post 3 includes in its top area a connecting element 7a and in the area below the connecting element 7a, it has a cylindrical portion 3a, which, in a downward direction, becomes narrower forming a truncated coneshaped area 3b. The rotational symmetrical axis of the mounting post 3 extends co-axially with the longitudinal axis 2 of the implant 1 and of the tooth when installed in the jaw bone.

On the mounting post 3, a crown 4 is disposed which is adapted to receive an artificial tooth or a prosthesis, neither one of which is shown herein. The crown 4 is disposed on the mounting post 3 and is adapted to receive and carry the artificial tooth structure or a prosthesis. The crown 4 has a double-truncated cone-shape with a lower truncated cone section 4a whose cross-section becomes smaller in downward direction along the longitudinal axis 2 and which is axially substantially shorter than the upper truncated cone section 4b whose cross-section becomes smaller in the upward direction. In the interior of the crown 4, there is a central cavity 4d, which in the present case is formed by a bore 4d which is co-axial with the longitudinal axis 2.

For interconnecting the crown 4 and the mounting post 3, a form-locking connection 7 is provided which in FIG. 1 is in the form of a bayonet lock. To this end, the mounting post 3 is cylindrical at its upper end and has a diameter which is somewhat smaller than the diameter of the central cavity 4d in the crown 4, so that the crown is longitudinally movable relative to the mounting post 3 in the direction of the axis 2. At the cylindrical upper end of the mounting post 3, there is a first connecting element 7a which is formed by two opposite rectangular projections with recesses extending radially from opposite sides into the projections. The top view of FIG. 1a shows the rectangular projections having straight outer edges, but the outer edges may be rounded that is the projections may be circular sections.

The first connecting element 7a of the mounting post can be brought into engagement with a second connecting element 7b of the crown which second connecting element is formed by an inner annular recess in the lower part of the crown 4. For the assembly of the mounting post 3 and the crown 4, the annular inwardly extending projection 7b of the crown 4, which is disposed below the first connecting element 7a, includes two openings corresponding to the rectangular projections of the first connecting element 7a of the mounting post 3 and into which the rectangular projections 7b extend. The height of the annular recess in the direction of the longitudinal axis 2 is at the openings so large that the rectangular projections of the first connecting element 7a can be rotated into the annular recesses. The height then becomes smaller in the direction of rotation in a ramp-like fashion up to an engagement recess, which, in the direction of rotation, is disposed in front of the next opening and serves as rotational locking structure. The opening has such a height in the direction of the longitudinal axis 2, that in the assembled state, limited movement of the crown 4 in axial direction with respect to the mounting post 3 is possible. The axial motion clearance depends on the height difference between the second connecting element 7b of the crown 4 and the first connecting element 7a of the mounting post 3 and is preferably 10 to 100 micrometer.

In the cylindrical space between the mounting post 3 and the crown 4 which is present in the assembled state a pretensioned spring element, 6 is disposed in the form of a spiral compression spring. The spring element 6 abuts a first engagement surface 6a at the upper end of the mounting post 6 and a second engagement surface 6b at the upper end of the central cavity 4d of the crown 4 so that the crown 4 is biased away from the mounting post 3 in the direction of the longitudinal axis 2 when it is not loaded. For the adjustment of the spring force spacer elements 6c may be placed between the spring element 6 and the engagement surfaces 6a and 6b.

At its lower end, the crown 4 includes a transition bore 4c so that, in an assembled state of the tooth implant part 1, the crown 4 extends over the cylindrical area 3a of the mounting post 3. In a non-loaded state, that is when no outer forces act on the tooth implant in the direction of the axis 2, the lower conical part 4a of the crown 4 and the frustroconical part 3b of the mounting post 3 are essentially in alignment so that the transition area 5 is sealed and food rests or cement used for mounting the prosthesis or for forming the crown cannot enter the interior of the implant part 1 and, as a result, block the movement of the crown 4 relative to the mounting post 3.

For installation, the assembled implant can be threaded into the basic carrier (not shown), which has been implanted into the jaw bone, via an inner cone wrench which is placed onto the crown 4 and pressed downward to engage the implant part 1 so as to permit its rotation. The crown may also be provided at its outside with grooves or with flattened areas so that it can be engaged by a suitable tool in a form-locking manner for example by way of a double edge or a hexagonal socket wrench.

It is a particular advantage that this implant 1 is easy to install and that the crown 4, mounted by a bayonet locking structure, can easily be removed from the mounting post in a non-destructive manner for control or repair purposes.

Figures 2, 2A:
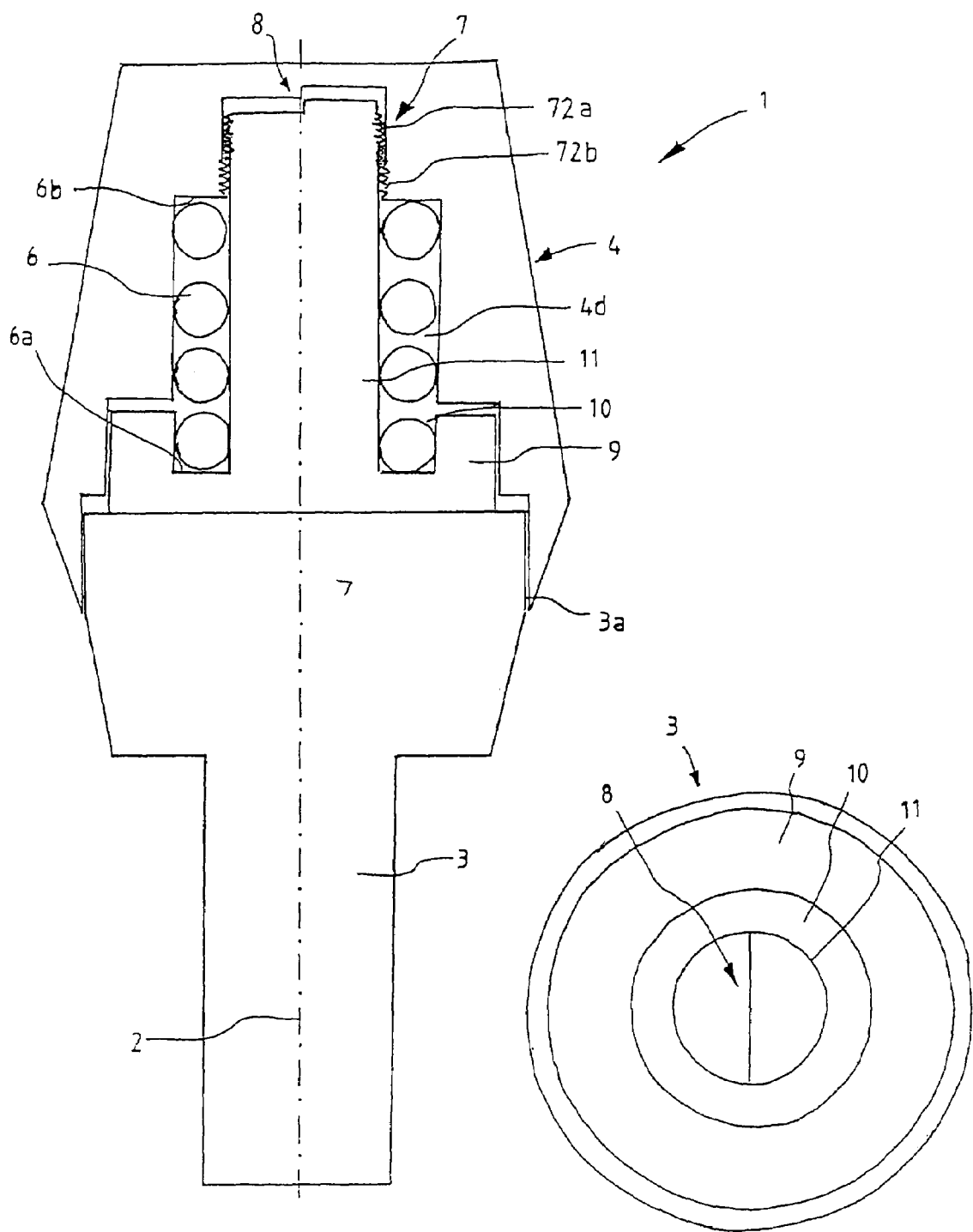
FIG. 2 is an axial cross-sectional view of a second embodiment of a dental implant wherein the implant part is threaded onto the mounting post.
FIG. 2a is a top view of the mounting post for an implant part as shown in FIG. 2.

FIG. 2 shows in a cross-sectional view taken along the longitudinal axis 2 an assembled implant part 1 with a thread joint and, FIG. 2a is a top view of the respective mounting post 3. This implant part 1 is to a large extent identical with the embodiment shown in FIG. 1 so that only those elements will be described below which are different from the embodiment shown in FIG. 1.

In this embodiment, the mounting post 3 includes above its cylindrical section 3a an outer cylinder 9 with an annular groove 10 and an inner cylinder 11 at the upper end of which a first connecting element 72 of the mounting post 3 is arranged.

The outer cylinder 9 extends co-axially with the longitudinal axis 2 and has a slightly smaller diameter than the cylindrical area 3a of the mounting post 3. It extends movably into a corresponding bore in the lower part of the crown 4. The outer cylinder 9 as well as the corresponding bore of the crown 4 have a smaller height than the central cavity 4d of the crown. The outer cylinder 9 is shorter than the corresponding bore in the crown 4 by an amount corresponding to the desired length of axial freedom of movement between the mounting post 3 and the crown 4.

The inner cylinder 11 extends co-axially with the longitudinal axis and projects into the central cavity 4d of the crown 4. The diameter of the inner cylinder 11 is so selected that a spring element 6 can be accommodated between the outer surface of the inner cylinder 11 and the inner surface of the central cavity 4d corresponding to the spring element shown in FIG. 1.

For a secure engagement of one end of the spring element 6 with the mounting post 3, the first support surface 6a for the spring element 6 is disposed in the annular groove 10 which is formed axially into the outer cylinder 9 around the inner cylinder 11. The second support surface 6b for the spring 6 is formed by an upper shoulder of the central cavity 4d in the crown 4.

In order to join the mounting post 3 and the crown 4 in a form-locking manner, an additional upwardly extending cylindrical connecting cavity extends co-axially with the longitudinal axis 2 upwardly into the crown 4 with a diameter which is slightly larger than that of the inner cylinder 11. The lower area of the connecting cavity includes an internal thread 72b, which forms a post connecting structure with the crown 4. The internal thread 72b fits with a corresponding outer thread 72a at the upper end of the inner cylinder 11 which represents the other part of the connecting structure on the mounting post 3. The crown 4 is mounted onto the mounting post 3 by threading the inner cylinder 11 with the outer thread 72a into the inner thread 72b of the crown 4 until the two threads are out of engagement. In order to facilitate this procedure and, additionally, the desired axial movement of the crown relative to the mounting post 3 the area of the connecting cavity above the internal thread 7b is as high as the outer thread plus the desired length of freedom of movement of the crown 4.

Further the connecting cavity includes at its top a semicircular recess into which a corresponding semicircular projection at the upper end of the inner cylinder 11 may extend. Together they form a rotational locking structure 8. They have a height which permits the desired movement of the crown 4 with respect to the mounting post 3 in the direction of the longitudinal axis 2 including the movement clearance. By downward pressing the screwed-in crown 4 onto the mounting post 3, the semi-circular recess comes into form-locking engagement with the semi-circular inner cylinder part so that the implant part 1 can be screwed into the basis carrier which has already been implanted into the jaw bone.

A particular advantage of the implant part 1 with the thread connection is that it is not only easy to install but that the crown 4 can easily be removed from the mounting post 3 for control or repair purposes without destroying it. Furthermore, the inner cylinder 11 provides for increased stability of the mounting post 3 and provides good guidance for the spring element 6 for which also more space in the direction of the longitudinal axis 2 is available.

FIG. 3 is a cross-sectional view along the longitudinal axis 2 of a composite tooth implant with an implant part 1 with a snap-in locking structure including an outer engagement member disposed on the mounting post. FIG. 3a is a top view of the respective mounting post. This implant part 1 differs from the embodiments shown in FIGS. 1 and 2 by the type of the connection which will be described below:

At its upper end, the mounting post 3 is provided with a hexagonal end post 15 which, starting at the cylindrical area 3a of the mounting post 3, becomes uniformly smaller in cross-section. The end post 15 however may have a shape other than hexagonal: it may have, for example, a triangular or a multi-angular cross-section. At the upper end of the hexagonal end post 15 engagement members 73a are provided which extend outwardly beyond the outer surfaces of the post 15 and have a lower horizontal engagement edge and an upper inclined ramp surface. A bore 16 is provided in the upper end of the hexagonal end post 15 which extends about halfway down the height of the hexagonal end post 15. The upper ends of the hexagonal end post 15 are provided with cut-outs 12, which essentially extend down almost to the bottom wall of the bore 16 so as to form six post legs. The bore walls sections separated by the cut-outs 12 provide for resiliency of the legs of the hexagonal end post 15 which form elastic latching elements.

The central cavity 4d of the crown 4 has at the bottom end a transition bore section 4c and above the transition bore section 4 three areas: A lower area of an upwardly narrowing hexagonal cross-section corresponding to the shape of the hexagonal end post 15; an intermediate area with inner engagement structures 73b, which have a horizontal engagement shoulder on which the elastic latch elements 73a of the legs of the mounting end post 15 snap out so as to provide for a secure connection between the mounting post 3 and the crown 4; and a third upper area of the central cavity 4d of the crown 4 comprising a cylindrical bore for receiving the spring element 6, which is disposed in the space between the central cavity 4d of the crown and the bore 16 in the mounting post 3.

In order to facilitate axial movement of the crown 4 relative to the mounting post 3 when the implant part 1 is assembled, the height of the transition bore 4c and the lower and intermediate area of the central cavity 4d of the crown 4 with respect to the height of the hexagonal end post 15 is so selected that the desired amount of movement can be accommodated.

In this embodiment, it is particularly advantageous that the implant part can be easily and rapidly assembled. The hexagonal end post 15 also prevents sideward movement of the crown 4 on the mounting post 3 and at the same time, prevents rotation of the crown 4.

Figure 4:
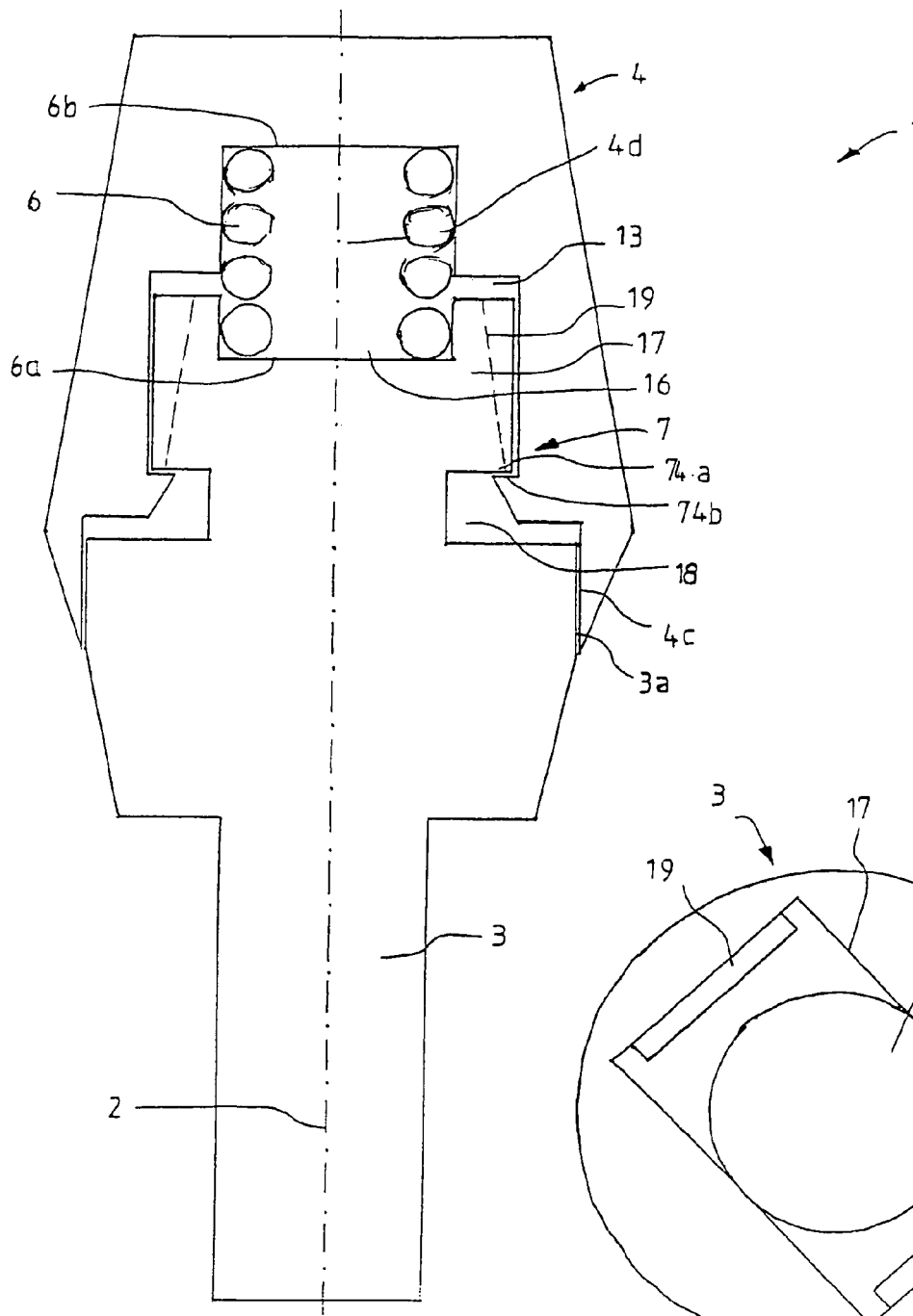
FIG. 4 is an axial cross-sectional view of a forth embodiment of a dental implant with a snap-lock structure including snap engagement members which are part of the dental implant part.
Figure 4A:
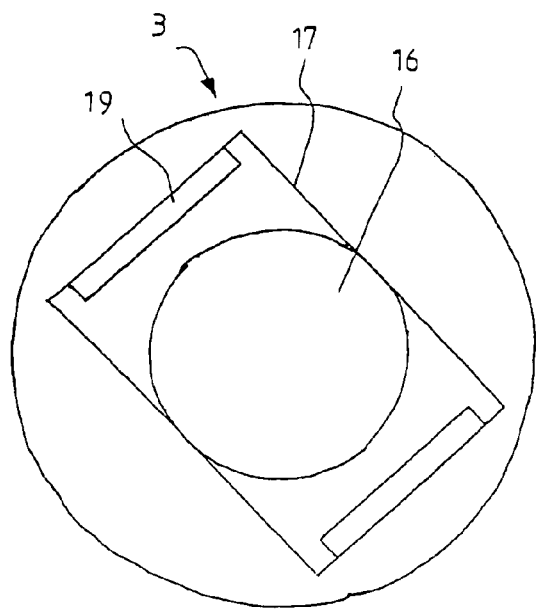
FIG. 4a is a top view of a mounting post for a dental implant part as shown in FIG. 4.

FIG. 4 is a cross-sectional view taken along the longitudinal axis 2 of a composite implant part, with a snap-lock latching mechanism between the crown 4 and the mounting post 3, and FIG. 4a is a top view of the respective mounting post 3. This implant part 1 differs from those of FIGS. 1 to 3 by the type of connection which will be described below.

The mounting post 3 comprises in the upper area thereof a rectangular end post 17 which, at its lower end adjacent the cylindrical section 3a of the mounting post 3, has two opposite recesses 18 whose upper surface areas form the horizontal engagement shoulder 74a for the snap connection. The side surfaces 19 of the more inwardly disposed sides of the rectangular post 17 are partially inclined inwardly toward the top of the mounting post in order to facilitate the engagement of the snap connection. The upper end of the rectangular end post 17 includes a bore 16 for receiving and supporting the spring element 6.

The central cavity 4d of the crown 4 includes above the transition bore 4c two areas; the lower area comprises a rectangular cavity section 13 which corresponds in shape to the rectangular end post 17. At the lower end, the cavity wall is provided with opposite engagement elements 74b each having an upper horizontal engagement edge and a lower ramp area which is inclined upwardly-inwardly. The second, upper area of the central cavity 4d of the crown is a cylindrical bore for receiving the other end of the spring element 6, which is disposed in the space formed by the center cavity 4d of the crown and the bore 16 in the mounting post 3.

In order to facilitate movement of the crown 4 relative to the mounting post 2 in the direction of the longitudinal axis 2 when the implant part 1 is assembled the heights of the transition bore 4c and the rectangular cavity section 13 of the central cavity 4d of the crown with respect to the heights of the respective opposite surfaces of the rectangular end post 17 are so selected that the desired movement can be accommodated.

In this embodiment, it is particularly advantageous that the implant part can be rapidly assembled in a simple manner. Furthermore, the rectangular end post 17 prevents sideward movement of the crown 4 on the mounting post 3 and at the same time prevents rotation of the crown 4.

Figures 5, 5A:
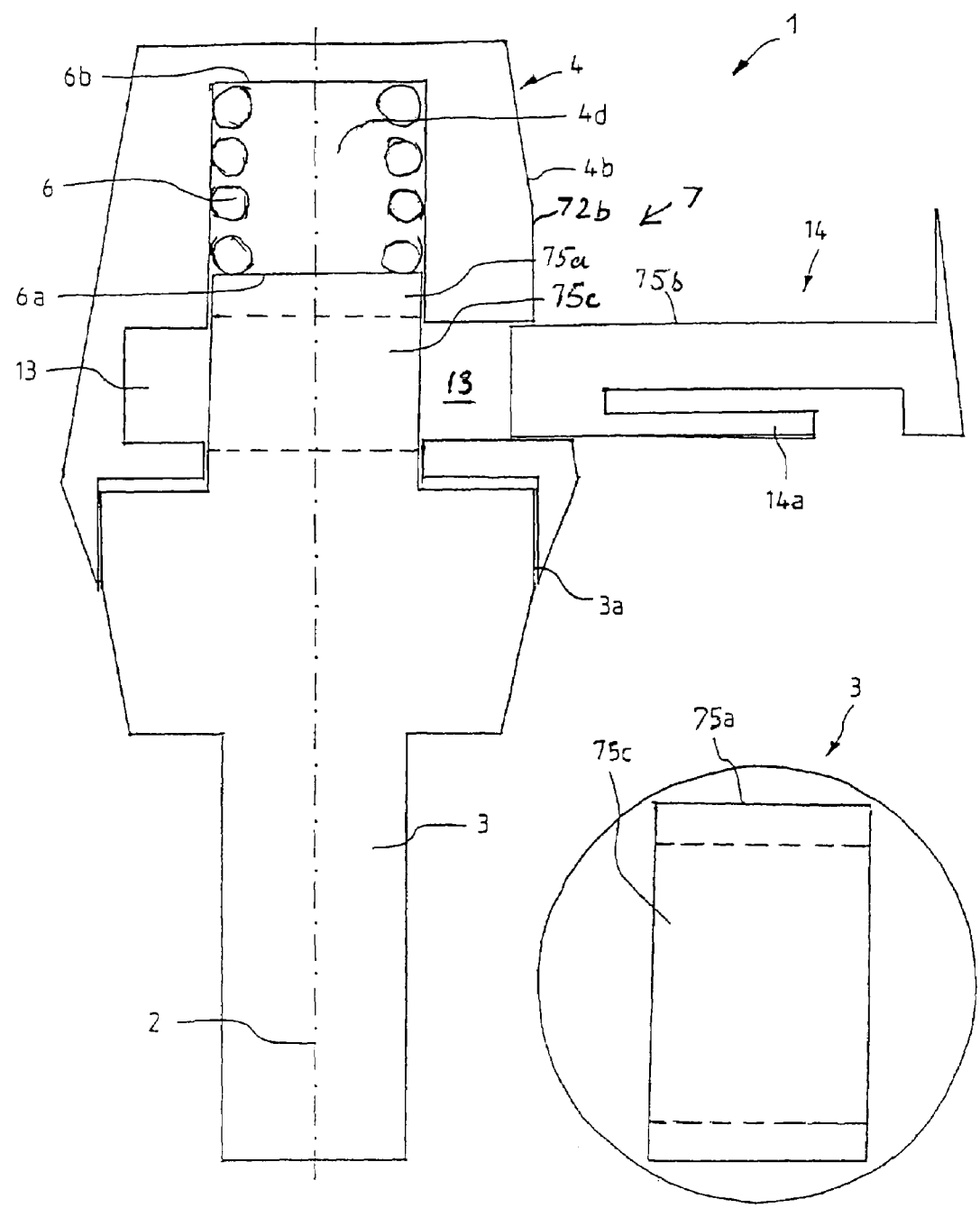
FIG. 5 is an axial cross-sectional view of a fifth embodiment of a dental implant with a slide locking element provided with a locking element.
FIG. 5a is a top view of a mounting post for a dental implant part as shown in FIG. 5.

FIG. 5 is a cross-sectional view taken along the longitudinal axis 2 of a composite implant part 1 with sidewardly removable locking members and FIG. 5a is a top view of the respective mounting post.

The form-locking connection 7 between the mounting post 3 and the crown 4 is realized by a sidewardly insertable mounting element 14. The connecting structure of the mounting post 3 is formed by the rectangular end post 75a which extends from the cylindrical area 3a of the mounting post 3 and has a rectangular passage 75c extending through the end post 75a transverse to the longitudinal axis 2.

The crown 4 is provided on an outer surface area at the upper truncated cone section 4b thereof with a flattened area 72b into which a rectangular side cavity 13 is formed which extends into the interior of the crown 4 and beyond the central cavity 4d of the crown 4. This rectangular side cavity 13 is, in the assembled state of the implant part 1 with the rectangular passage 75c of the mounting end post 75a.

The crown 4 and the mounting post 3 are interconnected by the safety element 14, which has essentially an elongated rectangular shape with a length so that, in the assembled state of the implant part 1, it extends through the rectangular side cavity 13 of the crown 4 and the rectangular opening 75c in the rectangular end post 75a up to the inner end of the rectangular side cavity 13. The height and width of the safety element 14 are so selected that it fits snugly into the rectangular cavity 13 of the crown 4 and a sideward movement of the crown 4 on the post 3 is prevented. The end of the safety element 14 which, in the assembled state of the implant part 1, faces outwardly complements the missing part of the crown 4 so that the crown's truncated cone-shape is re-established when the safety element 14 is inserted for locking the crown 4 to the mounting post 3.

In order to prevent an unintended release of the crown 4 from the mounting post 3, the safety element 14 includes at its bottom side a spring leaf 14a which is firmly connected at one end thereof to the safety element 14 and whose free end extend towards the outside wall of the crown 4. The leaf spring 14a extends in a released state with its free end so far beyond the underside of the safety element 14 that its free end comes into engagement with the top edge of the central cavity 4d of the crown at the rectangular opening 75c when the implant part 1 is assembled. In order to facilitate the insertion of the safety element 14 into the side cavity 13 of the crown 4 and through the rectangular opening 75c of the end post 75a, the leaf spring 14a may retract into a cut out in the underside of the safety slide element 14.

In order to support the crown 4 movably in the longitudinal direction 2 of the implant part 1 with respect to the mounting post 3, the rectangular opening 75c of the rectangular end post 75a is higher by the desired amount of movability between the crown 4 and the mounting post 3 than the safety element 14.

The first engagement surface 6a of the spring element 6 on the mounting post 3 is formed by the top side of the rectangular end post 75a, the second engagement surface 6b is formed by the top end of the central cavity of the crown 4. When the tooth implant is not loaded, the top side of the safety element 14 is pressed against the top side of the opening 75c of the rectangular end post 75a.

It is a particular advantage of the arrangement according to the invention that no central inner screw arrangement is needed for the connection of the mounting post and the crown and the spring element can be disposed directly between the mounting post and the crown. A division of the crown into two parts is therefore not necessary whereby the assembly of the implant part consisting of mounting post, crown and spring element is simplified and the mounting post can be more massive and stronger. As a result of this increased stability and the prevention of relative rotation between mounting post and crown the assembled implant part 1 can be screwed by a tool engaging the crown such as two edge-, a hexagonal or an inner cone wrench, in a simple manner into the basic carrier implanted into the jaw bone.

With the smooth jointure between the crown and the mounting post in the lower area of the crown furthermore, the penetration of cement is prevented by which a prosthesis or a cover is mounted onto the crown. As a result, the axial movability of the crown on the mounting post is ensured; the chances of a blockage are minimized.

What is claimed is:

1. A dental implant part (1) comprising a mounting post (3) which is cylindrical at its upper end and has a longitudinal axis (2), a crown (4) supported directly on the mounting post (3), and a spring element (6) supported coaxially with, and being disposed between, the mounting post (3) and the crown (4), such that the crown is movable within limits in axial direction relative to the mounting post (3), said crown (4) being connected to the mounting post (3) by an internal form-locking connection (7) in the form of a bayonet lock comprising a first connecting element which is formed by radial projections (7a) extending outwardly from the mounting post (3), and a second connecting element (7b) formed by an inner annular recess (8) in a lower part of the crown (4) for receiving the radial projections (7a) and defining an inner annular inwardly extending projection of the crown disposed below said first connecting element (7a), said second connecting element (7b) having openings corresponding to said radial projections (7a) of said first connecting element, to permit insertion of the radial projections (7a) axially into the annular recess (8) and means for preventing relative rotation of the mounting post (3) and the crown (4), the annular recess (8) having a height in the direction of the longitudinal axis (2) of the implant part (1) is at said openings so large that the projections of the first connecting element (7a) can be rotated into the annular recess, and the height then becomes smaller in the direction of rotation in a ramp-like fashion up to an engagement recess, which, in the direction of rotation, is disposed in front of the next opening and serves as a rotational locking structure.

2. A dental implant part according to claim 1, wherein the form-locking connection (7) is releasable so that the crown (4) can be removed from the mounting post (3) without damage.

* * * * *